(12) United States Patent
Pero (10) Patent No.: US 6,339,073 B1
(45) Date of Patent: Jan. 15, 2002

(54) USES OF NICOTINAMIDE ADENINE DINUCLEOTIDE AND ITS DERIVATIVES FOR TREATMENT OF MALIGNANT AND INFECTIOUS DISEASES

(75) Inventor: Ronald W. Pero, Lund (SE)

(73) Assignee: Oxigene, Inc., Watertown, MA (US)

( * ) Notice: Subject to any disclaimer, the term of this patent is extended or adjusted under 35 U.S.C. 154(b) by 8 days.

(21) Appl. No.: 09/149,998

(22) Filed: Sep. 9, 1998

Related U.S. Application Data (60) Provisional application No. 60/058,652, filed on Sep. 10, 1997.

(51) Int. Cl.$^7$ .................... A61K 31/70; C07H 19/207

(52) U.S. Cl. ........................ 514/47; 514/45; 514/46; 514/48; 514/52; 536/26.23; 536/26.24; 536/26.1

(58) Field of Search ................ 514/45, 47, 52, 514/46, 48; 536/26, 23, 26.1, 26.24

(56) References Cited

U.S. PATENT DOCUMENTS

| | | | | |
|---|---|---|---|---|
| 4,997,818 A | * | 3/1991 | McCaffrey et al. | 514/45 |
| 5,180,714 A | * | 1/1993 | Sufrin et al. | 514/46 |
| 5,608,047 A | * | 3/1997 | Sih | 536/26.26 |
| 5,679,648 A |   | 10/1997 | McCaffrey et al. | 514/46 |
| 5,700,786 A | * | 12/1997 | Watanabe et al. | 514/47 |

OTHER PUBLICATIONS

Althaus, F.R. and Richter, Ch., "ADP–Ribosylation of Proteins" *Enzymology an Biological Significance* Table of Contents, pp. XI–XVI, Springer–Verlag, Berlin Heidelberg New York London Paris Tokyo (Exhibit 4).

Ashamu, Goria, A., "Roles For Adenosine Ribose Hydroxl Groups In Cyclic In Cyclic Adenosin 5'–Diphosphate Ribose–Mediated $Ca^{2+Release\dagger}$" Biochemistry (1997) vol. 36: No. 31:9509–9517 (Exhibit 5).

Funaro, Ada, et al., "Involvement Of The Multilneage CD38 Molecule In a Unique Pathway Of Cell Activation And Proliferation"*The Journal of Immunology*(Oct. 15, 1990) vol. 145: No. 8, pp. 2390–2396 ( Exhibit 6).

Galione, Antony and White, Alison, "$Ca^{2+}$ Release Induced By Cyclic ADP–Ribose"*Trends in Cell Biology*(Dec. 4, 1994) vol. 4 pp. 431–436 (Exhibit 7).

Gilman, Alfred, G., "G Proteins And Dual Control Of Adenylate Cyclase" *Cell* ( Mar. 1984) vol. 36:577–579 (Exhibit 8).

Glick, David, L., "Primary Structure Of A Molluscan Egg–Specific NADase, A Second–Messenger Enzyme" *Cell Regulaltion*(Mar. 1991) vol. 2:211–218 (Exhibit 9).

Harrap, K.R. and Renshaw, J., "Intracellular Nucleotide Pools And Their Significance In Antimetabolite Therapy" *Antibiotics Chemother*(1980) vol. 28:68–77 (Exhibit 10).

Hellmich, Mark, R. and Strumwasser, Felix, "Purification And Characterization Of A Molluscan Egg–Specific NADase, A Second–Messenger Enzyme" *Cell Regulation*-(Mar. 1991) vol. 2:193–202 (Exhibit 11).

Hemmi, Hiromichi and Breitman, Theodore, R., "Induction By Retinic Acid Of NAD+–Glychydrolase Activity Of Myelomoncytic Cell Lines HL–60, THP–1 And U–937, And Fresh Human Acute Promyelocytic Cells In primary Culture" *Biochemical And Biophysical Research Communications*(Dec. 15, 1982) vol. 109, No. 3, pp. 669–674 (Exhibit 12).

Horsman, Michael, R., "Nicotinamide And Other Benzamide Analogs As Agents For Overcoming Hypoxic Cell Radiation Resistance In Tumors"*Acta Oncologica*(1995) vol. 34, No. 5, pp. 571–587 (Exhibit 13).

Howard, Maureen, et al., "Formation And Hydrolysis Of Cyclic ADP–Ribose Catalyzed By Lymphocyte Antigen CD38" *Science*(Nov. 12, 1993) vol. 262:1056–1059 (Exhibit 14).

Hua, Jianyi, et al., "Acidic And Neutralized Metoclopramide Formulations Sensitize Ionizing Radiation Induced Cytotoxicity In A Human Lung Adenocarcinoma Xenografted To Scid Mice" *Anti–Cancer Drugs*(1995) vol. 6:451–455 (Exhibit 15).

Kaufmann, Scott, H., "Specific Proteolytic Cleavage Of Poly (ADP–ribose) Polmerase: An Early Marker Of Chemotherapy–Induced Apoptosis" *Cancer Research*(Sep. 1, 1993). vol. 53:3976–3985 (Exhibit 16).

Kim, Hyuntae, et al., "Synthesis And Degradation Of Cyclic ADP–Ribose By NAD Glycohydrolases" *Science*(Sep. 3, 1993) vol. 261:1330–1333 (Exhibit 17).

Kontani, Kenji, et al., "NAD Glycohydrolase Specifically Induced By Retinoic Acid In Human Leukemic HL–60 Cells" *The Journal of Biological Chemistry*(1993) vol. 268, No. 23, pp. 16895–16898 (Exhibit 18).

Kumagai, Masa–aki, et al., "Ligation Of CD38 Suppresses Human B Lymphopoiesis" *J. Exp. Med.*(Mar. 1995) vol. 181:1101–1110 (Exhibit 19).

Lee, Herbert and Iglewski, Wallace, J., "Cellular ADP–Ribosyltransferase With The Same Mechaniam Of Action As Diphtheria Toxin And Pseudomanas Toxin A" *Proc. Natl. Acad. Sci. USA*(May 1984) vol. 81:2703–2707 (Exhibit 20).

Lee, Hon Cheung and Aarhus Robert, "ADP–Ribosyl Cyclase: An Enzyme That Cyclizes $NAD^+$ Into A Calcium–Mobilizing Metabolite" *Cell Regulation*(Mar. 1991) vol. 2:203–209 (Exhibit 21).

(List continued on next page.)

*Primary Examiner*—Gary Geist
*Assistant Examiner*—Howard V. Owens, Jr.
(74) *Attorney, Agent, or Firm*—Cobrin & Gittes (57) ABSTRACT

This invention provides a method of killing tumor cells or microorganisms which comprises contacting the tumor cells or the microorganisms with an amount of nicotinamide adenine dinucleotide (NAD) or its analogs effective to increase clonogenic toxicity of cells. This invention also provides a method of killing tumor cells or microoganisms in a subject which comprises administering an amount of nicotinamide adenine dinucleotide or its analogs effective to increase clonogenic toxicity of cells to the subject.

6 Claims, 8 Drawing Sheets

OTHER PUBLICATIONS

Lee, H.C., et al., "Cyclic ADP–Ribose And Its Metabolic Enzymes" *Biochimie*(1995) vol. 77:345–355 (Exhibit 22).

Lee, Hon Cheung, et al., "Structural Determination Of a Cyclic Metabolite Of $NAD^+$ With Intracellular $Ca^{2+}$–Mobilizing Activity" *The Journal of Biological Chemistry*(1989) vol. 264, No. 3, pp. 1608–1615 (Exhibit 23).

Lindahl, Tomas, et al., "Post–Translational Modification Of Poly (ADP–Ribose) Polymerase Induced By DNA Strand Breaks" *Reviews*(Oct. 1995) pp. 405–411 (Exhibit 24).

Lund, Frances, et al., "Murine CD38: An Immunoregulatory Ectoenzyne" *Immunology Today*(1995) vol. 16, No. 16, pp. 469–473 (Exhibit 25).

McGahon, Anne et al., "BCR–ABL Maintains Resistance Of Chronic Myelogenous Leukemia Cells To Apoptotic Cell Death" *Blood*(Mar. 1, 1994) vol. 83, No. 5, pp. 1179–1187 (Exhibit 26).

Okamoto, H., et al., "New Aspects Of The Physiological Significance Of NAD, Poly ADP–Ribose And Cyclic ADP–Ribose" *Biochimie*(1995) vol. 77;356–363 (Exhibit 27).

Olsson, Anders, et al., "Specific Binding And Uptake Of Extracellular Nicotinamide In Human Leukemic K–562 Cells" *Biochemical Pharmacology*(1993) vol. 45, No. 6, pp. 1191–1200 (Exhibit 28).

Pero, Ronald , W., et al., "Multiple Mechanisms Of Action Of The Benzamides And Nicotinamides As Sensitizers Of Radiotherapy: Opportunities For Drug Design" *Cancer Detection and Prevention*(1998) vol. 22(3);225–236 (Exhibit 29).

Pero, Ronald, W., et al., "Active Transport Of Nicotinamide And The Adenine Moiety Of NAD By Metabolically Controled NAD Catabolism" *Division of Biochemical Epidemiology, Prevention Medicine Institute of the Strang Clinic*pp. 378–385 (Exhibit 30).

Rusinko, Nancy, and Lee, Hon Cheung, "Widespread Occurrence In Animal Tissues Of An Enzyme Catalyzing The Conversion Of $NAD^+$ Into A Cyclic Metabolite With Intracellular $Ca^{2+}$–Mobilizing Activity" *The Journal of Biological Chemistry*(1989) vol. 264, No. 20, pp. 11725–11731 (Exhibit 31).

Satoh, Masahiko, S., et al., "Dual Function For Poly(ADP–Ribose) Synthesis In Response To DNA Strand Breakage" *Biochemistry*(1994) vol. 33:7099–7106 (Exhibit 32).

Schweitzer, C.M., et al., "Spectrophotometric Determination Of Clonogenic Capacity Of Leukemic Cells In A Semisolid Microtiter Culture System" *Experimental Hematology*(1993) vol. 21:573–578 (Exhibit 33); and Vindeløv, Lars, L., "Flow Microfluorometric Analysis Of Nuclear DNA In Cells From Solid Tumors And Cell Suspensions" *Virchows Arch. B Cell Path.*(1977) vol. 24:227–242. (Exhibit 34).

* cited by examiner

FIG. 7A
Untreated

FIG. 7B

FIG. 7C
NAD 300 μM

USES OF NICOTINAMIDE ADENINE DINUCLEOTIDE AND ITS DERIVATIVES FOR TREATMENT OF MALIGNANT AND INFECTIOUS DISEASES

This application claims benefit of U.S. Provisional Application No. 60/058,652, filed Sep. 10, 1997, the content of which is incorporated into this application by reference.

Throughout this application, various references are referred to within parentheses. Disclosures of these publications in their entireties are hereby incorporated by reference into this application to more fully describe the state of the art to which this invention pertains.

BACKGROUND OF THE INVENTION

NAD and NADP are naturally occurring energy sources in cells. They are important cofactors to numerous enzymatic reactions. They are also substrates for NAD(P)ases which catalytically break down these products into nicotinamide and ADP-ribose or ADP-ribose phosphate. In addition, NAD is also a substrate for poly (ADP-ribose) polymerase and mono (ADP-ribose) transferases important in DNA repair, apoptosis, differentiation and signal transduction (Althaus & Richter, ADP-ribosylation of Proteins: Enzymology and Biological Significance, Springer-Verlag, Berlin, 1987; Satoh et al., Biochemistry 33: 7099–7106, 1994; Kaufman et al., Cancer Research 53: 3976–3985, 1993; Lindahl et al., TIBS 20: 405–411, 1995; Gilman AG, Cell 36: 577–579, 1984; Lee and Iglewski, Proc. Natl. Acad. Sci. USA 81: 2703–2707, 1984).

There are no known useful functions for the NAD(P)ases in cells: A group of NADases also possess ADP-ribosyl cyclase and cyclic ADP-ribose hydrolase activities (Galione and White, Trends in Cell Biol. 4:431–436, 1994; Lee et al, Biochemie 77: 345–355, 1995).

These enzymes were first described in sea urchin eggs and they have been purified (Rusinsko and Lee, J. Biol. Chem. 264: 11725–11731, 1989; Lee and Aarhus, Cell Regul. 2: 203–209, 1991; Hellmich and Stumwasser, Cell Regul 2:193–203, 1991) and cloned (Glick et al., Cell Regul 2: 211–218, 1991). The NAD hydrolyzing properties are coupled to synthesis of cyclic ADP-ribose (cADPR) (Lee et al. J. Biol. Chem. 264: 1608–1615, 1989), which has been shown to have secondary messenger properties involved in the induction of $Ca^{2+}$ release (Galione and White, Trends in Cell Biol. 4:431–436, 1994; Lee et al, Biochemie 77: 345–355, 1995).

Some of these enzymes are bifunctional having both ADP-ribosyl cyclase and cADPR hydrolase activities, and consequently can both synthesize cADPR or hydrolyze cADPR to ADP-ribose (Kim et al., Science 261:1330–1333, 1993; Lee et al, Biochemie 77: 345–355, 1995; Galione and White, Trends in Cell Biol. 4:431–436, 1994). One of these bifunctional enzymes is the CD38 ectoenzyme in mammalian B- and T-lymphocytes and myeloid cells (Lund et al., Immunol. Today 16: 469–473, 1995) and in insulin secretory human β-cells (Okamoto et al., Biochimie 77:356–363, 1995). The CD38 receptor has been shown via $Ca^{2+}$-release to be involved in the regulation of B cell proliferation (Howard et al., Science 262:1056–1059, 1993; Kumagai et al., J. Exp. Med. 181: 1101–1110, 1995), in T, NK and plasma cell regulation (Funaro et al., J. of Immunology 145: 2390–2396, 1990) and it is upregulated in HL-60 cells stimulated to differentiate by retinoic acid (Kontani et al., J. Biol. Chem. 268:16895–16898, 1993). Earlier it has also been shown (Hemmi and Breitman, Biochem. Biophys. Res. Com. 109: 669–674, 1982) that treatment with retinoic acid induced NADase activity in the same cell line, indicating a strong coupling between NADase- and CD38/cyclase activity.

NADase/cyclase is an ectoplasmically located cellular enzyme. Hence, when cells are supplied with NAD or NADP they can serve both (i) as substrates for the production of cyclic ADP-ribose, imbalance $Ca^{2+}$ and induce cytotoxicity and (ii) as a catabolic source for the generation of nicotinamide which can increase tumor blood flow. Both the apoptotic cytotoxicity and enhanced tumor blood flow are well documented mechanisms by which conventional radio- and chemotherapies can be sensitized (Pero et al, Cancer Det. Prevent. 22(3): 225–236, 1998; Horsman, Acta Oncologica 34: 571–587, 1995). It follows then that NAD and NADP are novel antitumor drugs because they can combine two important mechanisms of action into the same compound by acting as a metabolic prodrug.

Further to this invention is the disclosure that ADP-ribose cyclases such as CD38 are important metabolic sites for the expression of the desired pharmacological effects of NAD. Therefore, agents that can serve as precursors or metabolic products of NAD and NADP judged by their abilities to interact with cyclases should also be considered appropriate to this invention. For example, but not limited to, there are the metabolites and substrates such as cyclic ADP-ribose, ADP-ribose, 2' and 3' deoxy NAD, 2' and 3' deoxy ADP-ribose, NADH, and NADPH (Gailone and White, Trends in Cell Biology 4: 431–436, 1994; Ashamu et al, Biochemistry 36: 9509–9517) as well as other affinity binding agents to ADP-ribose cyclases (NADases) such as 3-acetyl pyridine adenine dinucleotide, 3-acetyl pyridine, nicotinamide mononucleotide, benzamide and 3-aminobenzamide (Olsson et al, Biochem. Pharmacol. 45:1191–1200, 1993).

SUMMARY OF THE INVENTION

This invention discloses a method by which agents such as NAD and NADP, or its metabolic precursors, products, and competitive substrates which agonize/antagonize ADP-cyclase and produce or inhibit cyclic ADP ribose and in turn imbalance intracellular calcium are useful in inducing or inhibiting apoptosis or clonogenic cytotoxicity in tumor, microorganism, or normal cells. In this regard, tumor cells for example having a high proliferative capacity are forced into a pathway of differentiation and eventual apoptotic cell death. Because the large majority of normal tissues of the body are not undergoing cell division, a therapeutic gain of killing tumor tissues over normal tissues is realized. The useful method is comprised of the steps of administering by an appropriate route (e.g. intravenous, oral, intramuscular) to a patient having a tumor, NAD or NADP at a dose sufficient to elevate cyclic ADP ribose, imbalance calcium and induce apoptotic cytotoxicity, so that proliferating tumor cells are inhibited to grow.

In another aspect, this invention teaches that treating individuals having tumors with therapeutic doses of NAD or NADP or an appropriate analog will not only kill tumor cells by apoptosis, but the enzymatic product of this process, cyclic ADP(P)ribose, also results in the production of another well known radio- and chemosensitizer, nicotinamide. Consequently, combining NAD or NAD(P) with conventional radio- or chemotherapies permits sensitization by both the apoptotic as well as nicotinamide cytotoxic mechanisms (i.e. increasing tumor blood flow; Horsman, Acta Oncologica 34: 571–587, 1995). Hence, the method taught by this invention may be augmented by co-administering to the tumor patient traditional radio- or chemotherapies in combination with useful formulations of NAD and NADP as a sensitizing adjuvant therapy.

In still another aspect, this invention teaches that NADases or ADP-ribose cyclases could also be viewed as a transport mechanism for internalizing into cells phosphorylated adenosine-containing precursors for eventual use in DNA synthesis. It is known that the ADP-ribose moiety of NAD becomes selectively taken up by cells when supplied with exogenous NAD (Pero et al, In: ADP-ribose transfer reactions. Biological significance, Eds. M. K. and E. L. Jacobson, pp 378–385, Springer, N.Y., 1989). Stimulating ATP synthesis selectively would no doubt imbalance nucleotide pools and provide opportunities for antimetabolite therapy (Harrup and Renshaw, Antibiotics Chemother. 28: 68–77, 1980). Adenosine compounds, some of which can imbalance nucleotide pools by inhibition of adenosine deaminase such as coformycin and deoxycoformycin, have been used for the successful treatment of neoplastic, fungal and parasitic diseases (Harrup and Renshaw, Antibiotics Chemother. 28: 68–77; U.S. Pat. Nos.: 5,180,714; 4,997,818; 5,679,648). Here I disclose that adenosine-containing analogs that can bind to the ectoplasmically located NADases (ADP-ribose cyclases) and become internalized into the cell and imbalance nucleotide pools have utility in the treatment of neoplastic, fungal and parasitic diseases.

DETAILED DESCRIPTION OF DRAWINGS

DETAILED DESCRIPTION OF THE INVENTION

This invention provides a method of killing tumor cells or microorganisms which comprises contacting the tumor cells or the microorganisms with an amount of nicotinamide adenine dinucleotide (NAD) or its analogs effective to increase clonogenic toxicity of said cells or microorganisms. In an embodiment, the microorganisms is a fungus or a parasite.

As used herein, the NAD analogs include, but are not limited to metabolic precursors or products of nicotinamide adenine dinucleotide, or metabolic substrate inhibitors of nicotinamide adenine dinucleotide. Examples are NADP, NADH, NADPH, ADP-ribose, 3'-deoxy ADP ribose, 2' and 3'-deoxy NAD, 3'-deoxy NADP, 2' and 3'-deoxy ADP-ribose and other modifications of NAD that can serve as a substrate for ADP-cyclase/ NADases as well as compounds that can bind to the metabolic site such as cyclic ADP-ribose, ADP-ribose (Gailone and White, Trends in Cell Biology 4: 431–436, 1994; Ashamu et al, Biochemistry 36: 9509–9517) as well as other affinity binding agents to ADP-ribose cyclases (NADases) such as 3-acetyl pyridine adenine dinucleotide, 3-acetyl pyridine, nicotinamide mononucleotide, benzamide and 3-aminobenzamide (Olsson et al, Biochem. Pharmacol. 45:1191–1200, 1993).

This invention also provides a method of killing tumor cells or microorganisms in a subject having the tumor cells or the microorganisms which comprises administering to the subject an amount of nicotinamide adenine dinucleotide or its analogs effective to increase clonogenic toxicity of said cells or microorganisms. In an embodiment, the subject can be an animal. In another embodiment, the subject is a human.

"Administering" means any of the standard methods of administering a compound to a subject, known to those skilled in the art. Examples include, but are not limited to intravenous, intramuscular or intraperitoneal administration.

The clonogenic toxicity may be increased by imbalancing $Ca^{2+}$ cytosolic levels or nucleotide pools or in combination thereof.

This invention also provides uses of NAD or its analogs for preparation of a medicament which comprises an amount of NAD or its analogs effective to increase clonogenic toxicity of cells or microorganisms.

This invention further provides use of NAD or its analogs for killing tumor cells or microorganisms.

This invention also provides a composition for killing tumor cells or microorganisms which comprises an amount of nicotinamide adenine dinucleotide or its analogs effective to increase clonogenic toxicity of said cells or microorganisms and a suitable carrier.

This invention further provides a pharmaceutical composition for killing tumor or infectious cells which comprises an amount of nicotinamide adenine dinucleotide or its analogs effective to increase clonogenic toxicity of cells and a pharmaceutically acceptable carrier.

For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing Polysorb 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

This invention further provides a method of treating neoplastic, fungal and parasitic diseases administering to a subject effective amount of the pharmaceutical composition comprising an amount of nicotinamide adenine dinucleotide or its analogs effective to increase clonogenic toxicity of cells.

Methods of determining an "effective amount" are well known to those skilled in the art and depend upon factors including, but not limited to: the size of the patient and the carrier used.

In an embodiment of the above compositions, the clonogenic toxicity is increased by imbalancing $Ca^{2+}$ cytosolic levels or nucleotide pools or in combination thereof.

In a further embodiment of the compositions, the nicotinamide adenine dinucleotide analog is a metabolic precursor or product of nicotinamide adenine dinucleotide, or metabolic substrate inhibitors of nicotinamide adenine dinucleotide.

This invention also provides a kit comprising an compartment containing an amount of nicotinamide adenine dinucleotide or its analogs with the tumor cells or the microorganisms effective to increase clonogenic toxicity of tumor cells.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Cell culture. HL60 (human promyeloid leukemia line) cells were cultured at a density of $0.5 \times 10^6$ to $1.0 \times 10^6$ cells/ml in RPMI medium supplemented with 10% fetal calf serum (FCS) at 37° C. in a 5% $CO_2$ atmosphere. The cells were harvested by centrifugation and resuspended in fresh medium at a concentration of $1 \times 10^6$ to $2 \times 10^6$ cells/ml for bioassay purposes.

Measurement of in vitro cytotoxicity by apoptosis. HL60 cells were exposed in culture to 2 Gy radiation, 100 μM nMCA (neutral metoclopramide, Neu-Sensamide), 0–5000 μM NAD±10 mM, and±NADase inhibitor, 3-acetyl pyridine adenine dinucleotide, given 30 minutes before drug treatment. The % apoptosis was determined after 6 hours. The cytotoxicity was evaluated by morphological identification of apoptotic cells (400 ×magnification with phase contrast microscopy) using trypan blue exclusion (0.1% isotonic solution+5% serum) after 5 minutes incubation at room temperature. Apoptotic cells were identified as having chromatin condensation, shrinkage, membrane blebbing, fragmentation and appearance of "apoptotic bodies" (Kaufman et al, Cancer Res. 53:3976–3985, 1993). Necrotic cells were identified as cells that did not exclude trypan blue.

Assessment of cytotoxicity in HL60 and K562 cells by clonogenic assay. The assay used is based on Schweitzer et al (Exper. Hematol. 21: 573–578, 1993). HL60 or K562 cells were cultured in 96-well microplates, at 800 cells per well, in a medium of 0.6% methyl cellulose (Methocel A4M, Dow Chemicals, USA), 10% fetal calf serum, RPMI 1640 (Life Technologies Ltd, UK), and gentamycin (50 μg/ml, Biological Industries, Israel). Microculture wells received 10 μl of NAD, NADP, NADH, ADP-ribose, nicotinamide (NAM), or 3-acetyl pyridine adenine dinucleotide solutions within which the final concentrations were adjusted to be between 0–5000 μM after addition of 190 μl cell-containing medium. Final methyl cellulose concentration was 0.6%. The cells were incubated at 37° C. in 5% $CO_2$ for 7 days, then assayed microscopically for the number of cell colonies (>40 cells) and clusters (8–40 cells). In the case of the radiosensitization experiments, the cells were irradiated with 1–2 Gy gamma radiation 15 minutes before addition of NAD. The central area of the bottom of each well (25% of total) was counted, and the counts of colonies and clusters expressed as % of control in order to avoid influences from inter-experimental baseline variations.

Estimation of cycle arrest in 70Z/3 mouse preB/B tumor cells. The procedure was according to Vindelöv (Virchows Archives Cell Pathology 24:277, 1977). Briefly, cells were exposed in culture at 37 C to ±300 μM NAD for 16 hours before they were collected by centrifugation and suspended in a buffered solution containing NP-40 detergent, RNase A and propidium iodide. Propidium iodide intercalates into double stranded DNA and can be measured by fluorescence using flow cytometry. The NP-40 lyzes plasma membranes and the RNase prevents interference caused by RNA staining. Cells in G2/M will have twice the amount of DNA and hence fluorescence as cells in G0/G1. Cells in S-phase are located in the histogram between the G0/G/1 and G2/M peaks.

Evaluation of antitumor activity of NAD in vivo. Scid mice (n=10 per group) were transplanted by subcutaneous injection of H-2981 (human adenocarcinoma) tumor tissue suspension in the right flank. When the tumors grew to 80–100 mm2, the animals were divided into three groups: Group 1 was injected i.p. with saline, Group 2 was injected i.p. with NAD at 25 mg/kg dissolved in saline, and Group 3 was injected i.p. with NAD at 50 mg/kg. The treatment schedule was daily Monday through Friday with no treatment Saturday and Sunday for 21 days. Tumor volumes were recorded every other day for 21 days and converted to AUC tumor growth values as previously described in detail (Hua et al, Anti-Cancer Drugs 6: 451–455, 1995).

EXAMPLE 1

Figure 1:
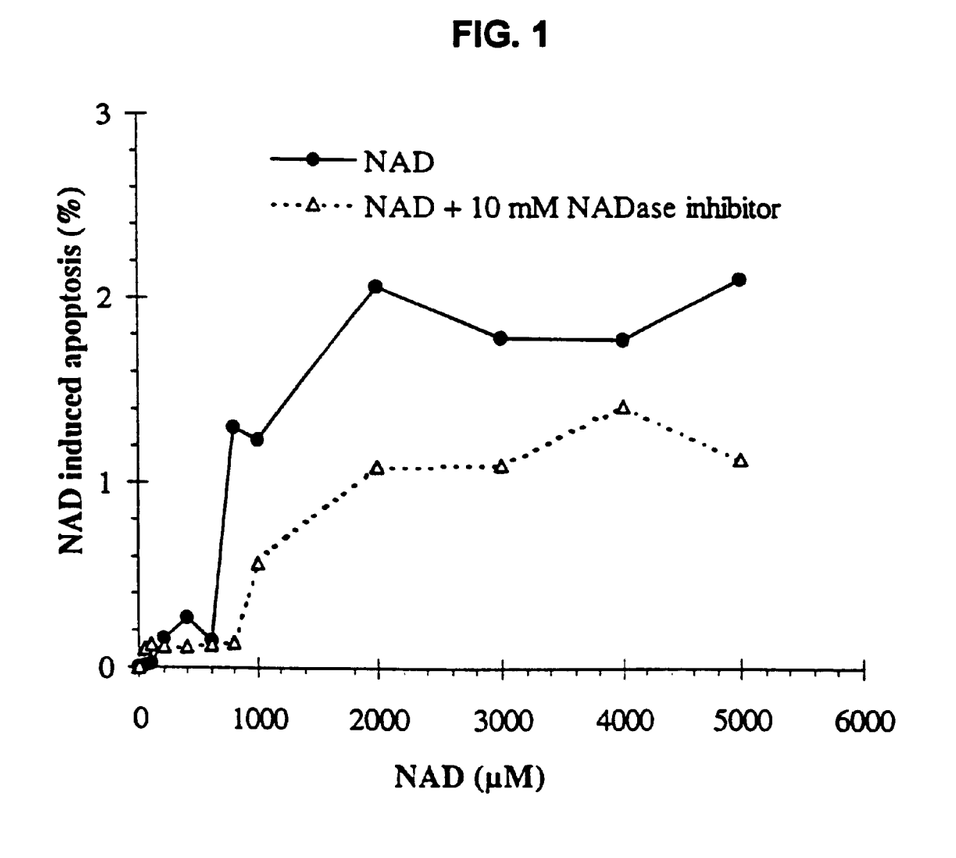
FIG. 1. Dose response of NAD in HL60 (promyeloid leukemia) cells evaluated by the induction of apoptosis in the presence or absence of 10 mM NADase inhibitor, 3-acetyl pyridine adenine dinucleotide. Untreated control levels of apoptosis were subtracted as background for all reported values.

FIG. 1 displays the result of exposing HL60 cells to increased doses of NAD±the presence of an NADase inhibitor. The data teach that NAD induces a dose dependent induction of apoptosis which in turn requires active NADase/cyclase, as evidenced by the striking inhibition of apoptosis by the presence of the NADase inhibitor, 3-acetyl pyridine adenine dinucleotide. Because NAD, NADP and the NADase inhibitor are substrates for the NADase/cyclase, and because the NADase inhibitor is used in considerable molar excess, then it becomes clear that NAD is substrate inhibited for the NADase/cyclase. Since NAD and NADP can generate cyclic intermediates and not 3-acetyl pyridine adenine dinucleotide, it is obvious that production of cyclic ADP-ribose is necessary for inducing apoptosis and not just a modulation of the NADase/cyclase activity. NADase/cyclase substrates that do not modulate cyclation leading to $Ca^{2+}$ imbalance would not be expected to have antitumor properties.

EXAMPLE 2

Figure 2:
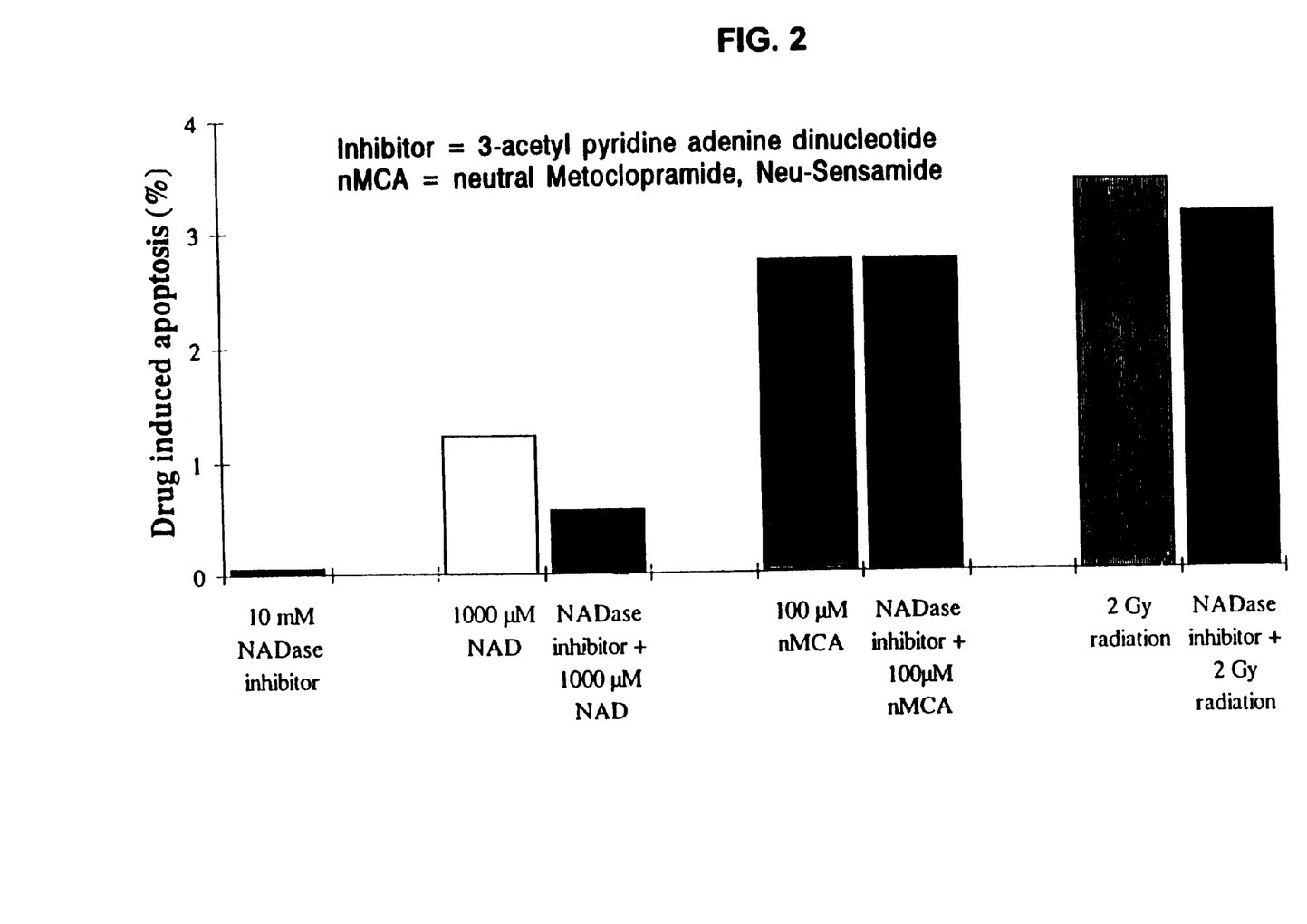
FIG. 2. Drug induced apoptosis in HL60 (promyeloid leukemia) cells treated with 1000 $\mu$M NAD, 100 $\mu$M nMCA (neutral metoclopramide, Neu-Sensamide), and 2 Gy radiation in the presence and absence of 10 mM NADase inhibitor, 3-acetyl pyridine adenine dinucleotide. Untreated control levels of apoptosis were subtracted as background for all reported values.

This example teaches two important points. Firstly, although the NADase inhibitor, 3-acetyl pyridine adenine dinucleotide, is a substrate for the ectoplasmic NADase/cyclase it cannot induce cytoxicity by apoptosis (FIG. 2). Secondly, NAD which is also a substrate for the NADase/cyclase, differs from 3-acetyl pyridine adenine dinucleotide in that it produces cyclic ADP-ribose which can imbalance cytosolic calcium resulting in apoptosis, and this induction is inhibited when the cyclase activity is competed for by the NADase inhibitor (FIG. 2). On the other hand, nMCA (neutral metoclopramide, Neu-Sensamide) and radiation which are both well known to induce apoptosis (Pero et al, Cancer Det. Prevent. 22(3): 225–236,1998), are unaffected by the presence of the NADase inhibitor. These data clearly indicate that the mechanism of induction of apoptosis by conventional agents such as radiation or nMCA are by different mechanisms than the NAD effects on apoptosis.

EXAMPLE 3

Figure 3A:
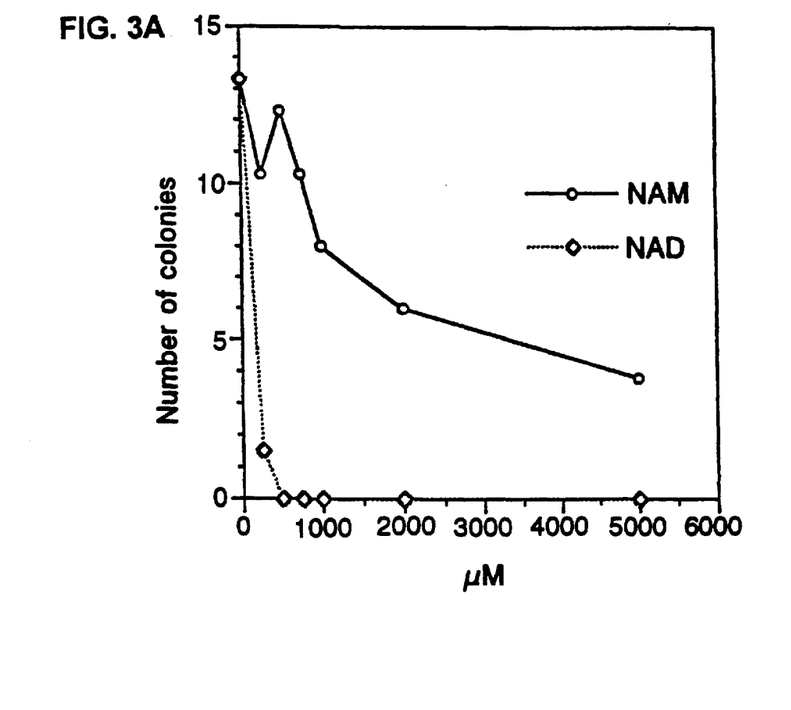
FIGS. 3A and 3B. Human HL60 (promyeloid leukemia) cell colonies (A) and clusters (B) grown in 0.6% methylcellulose, RPMI 1640 medium with 10% fetal calf serum, and supplemented with nicotinamide or NAD at the indicated concentrations for 6 days in 5% $CO_2$ at 37° C.
Figure 3B:
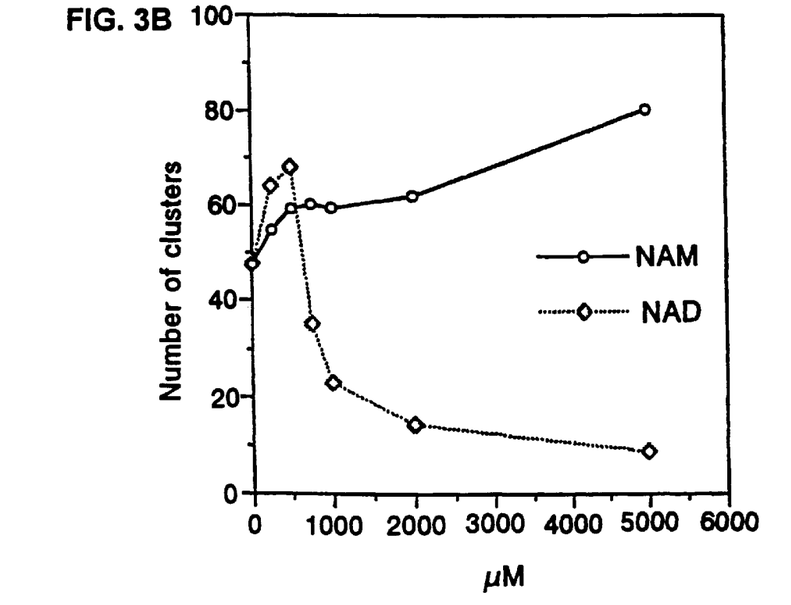
Figure 4A:
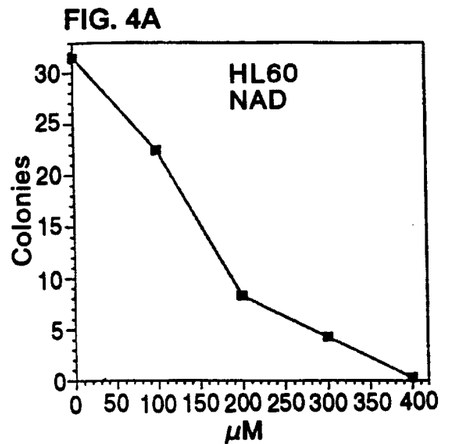
FIGS. 4A–4E. Clonogenic cytotoxicity of HL60 and K562 leukemic cells treated in vitro for 7 days in 5% $CO_2$ at 37° C. with 0–2000 (M doses of NAD, ADP-ribose and nicotinamide (NAM). The number of colonies (>40 cells) formed were counted microscopically in 96-well, flat-bottomed microculture plates. Note that the $IC_{50}$ dose response curves for clonogenicity of HL60 and K562 cells were the same after treatment with either NAD or ADP-ribose.
Figure 4B:
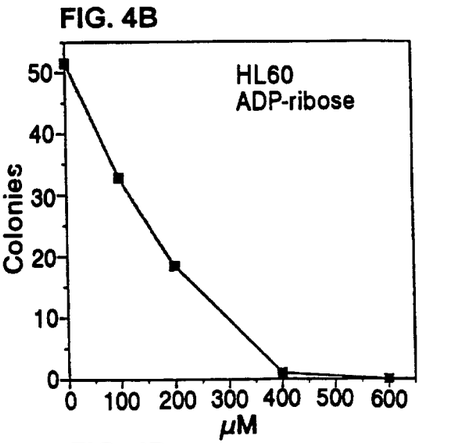
Figure 4C:
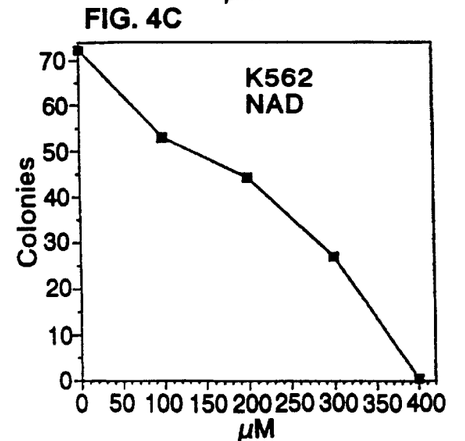
Figure 4D:
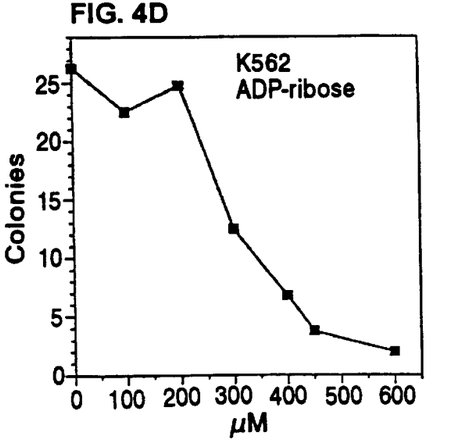
Figure 4E:
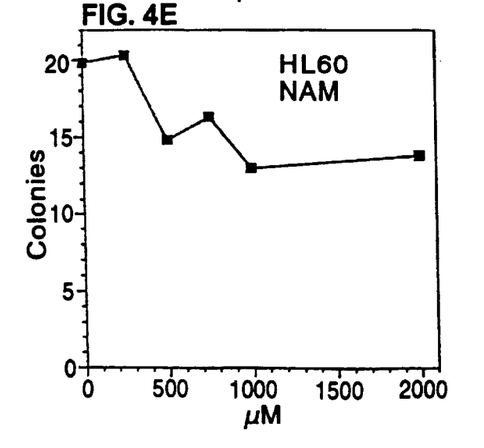
Figure 5A:
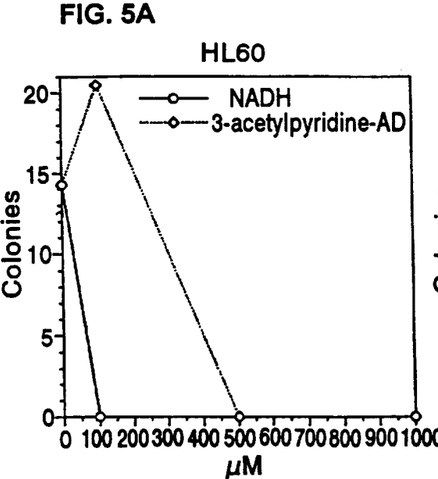
FIGS. 5A–5C. Clonogenic cytotoxicity of HL60 and K562 leukemic cells treated in vitro for 7 days in 5% $CO_2$ at 37° C. with 0–1000 (M doses of NADH, NADP and 3-acetyl pyridine adenine dinucleotide (3-acetylpyridine AD). The number of colonies (>40 cells) formed were counted microscopically in 96-well, flat-bottomed microculture plates.
Figure 5B:
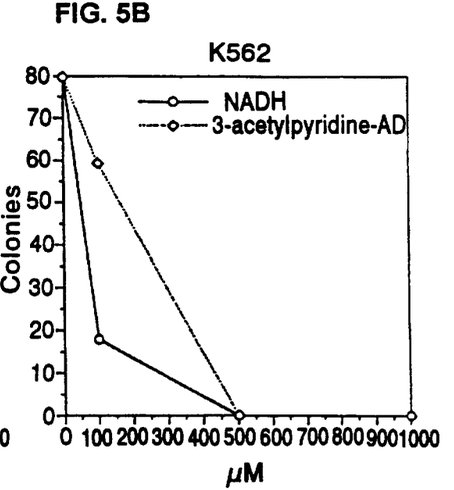
Figure 5C:
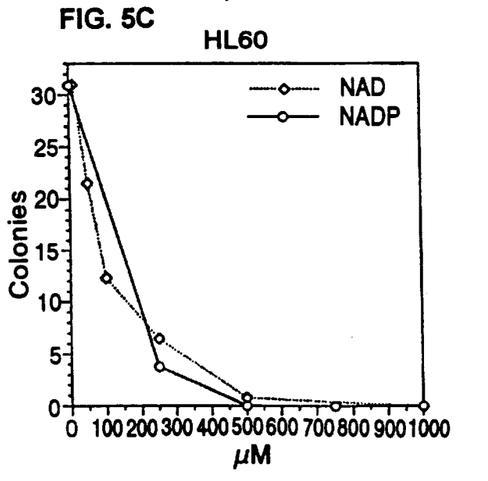

The data presented in FIGS. 3A and 3B confirms the important point that NAD which induces apoptosis also results in potent cytotoxicity of clonogenic tumor cells. Doses of NAD<500 µM result in>50% inhibition of clonogenicity. Nicotinamide (NAM) is itself an inhibitor and also another product of NADase/cyclase activity, but it has little to no effect on clonogenicity. These data disclose the therapeutic value of using NAD as a prodrug to improve the antitumor properties of agents. NAD can kill clonogenic tumor cells by producing cyclic ADP-ribose that mediates $Ca^{2+}$ imbalance, and at the same time produce nicotinamide a well known enhancer of tumor blood flow that can sensitize radio- and chemotherapies. These properties represent additive non-competing mechanisms for sensitization of tumor cytotoxicity.

EXAMPLE 4

The data presented in FIGS. 4A–4E and 5A–5C teach three important points about this invention. First, both metabolic precursors such as NADH or metabolic products such as ADP-ribose are equally effective at inducing cytotoxicity in clonogenic tumor cells. Second, tumor cells other than HL60, which in this case were K562 cells, were killed with equal proficiency. This was true even though it is known that HL60 leukemic cells are known to readily undergo apoptosis whereas K562 leukemic cells are known to be much more resistant to apoptosis (McGahon et al Blood 83: 1179–1187, 1994). Hence, the fact that NAD and ADP-ribose have similar dose response curves in HL60 and K562 cells teaches that these agents do not induce apoptosis and cytotoxicity by conventional apoptotic pathways known for most agents but by a unique independent pathway. Third, 3-acetyl pyridine adenine dinucleotide, although not a known producer of cyclic ADP-ribose, can nonetheless show cytotoxicity to clonogenic HL60 or K562 cells. These data disclose substrate inhibitors of NADases (ADP-ribose cyclases) which can induce clonogenic cytotoxicity are likewise useful for the treatment of proliferative disorders such as cancer.

EXAMPLE 5

Figure 6A:
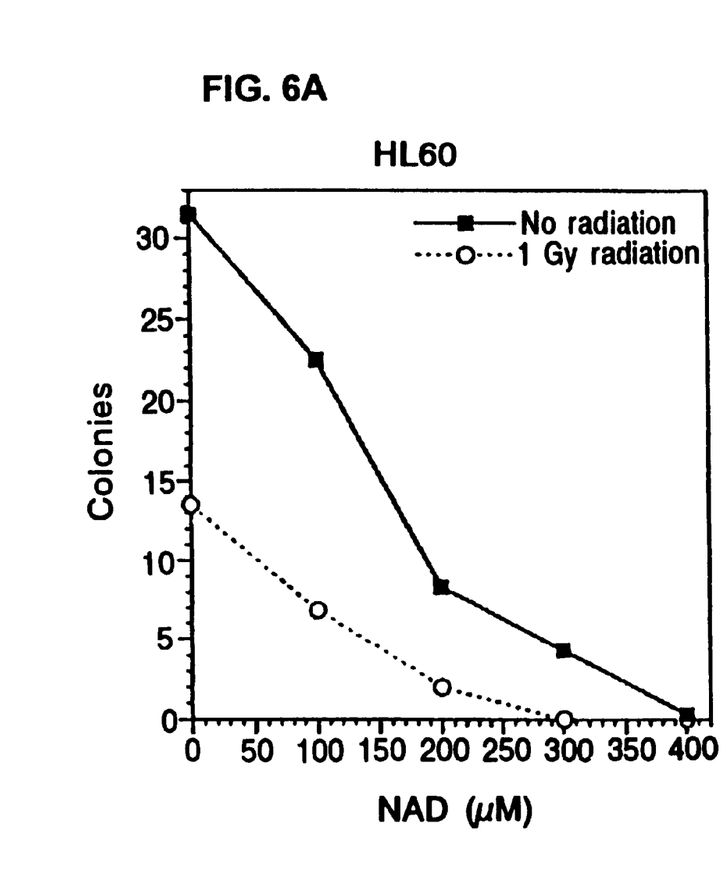
FIGS. 6A and 6B. Radiosensitization of HL60 and K562 leukemic cells by 0–300 (M NAD. Cells were first irradiated with 1–2 Gy and 15 minutes later incubated with the indicated concentrations of NAD for 7 days in 5% $CO_2$ at 37° C. The number of colonies (>40 cells) formed were counted microscopically in 96-well, flat-bottomed microculture plates.
Figure 6B:
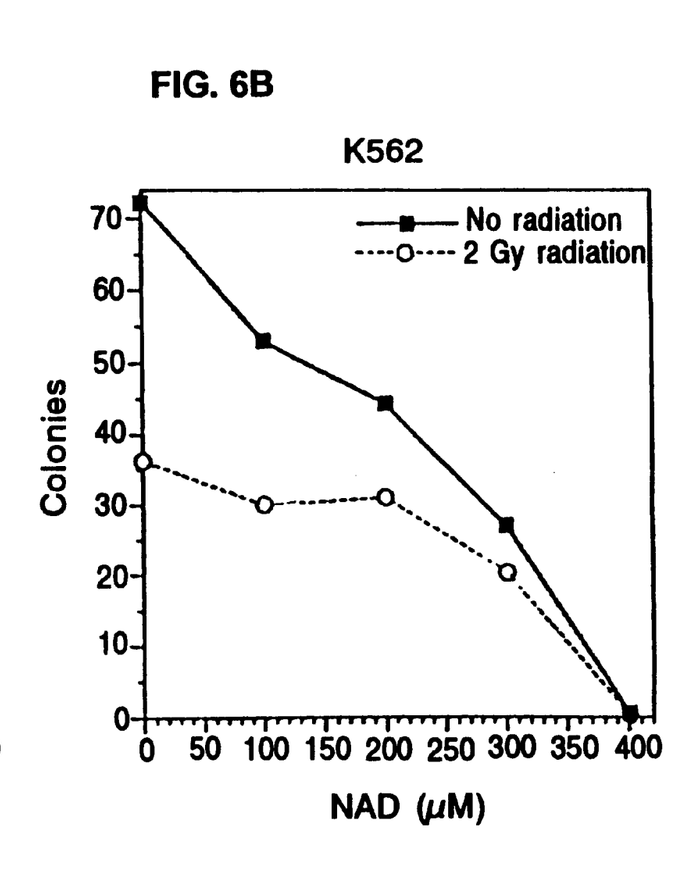
Figure 7A:
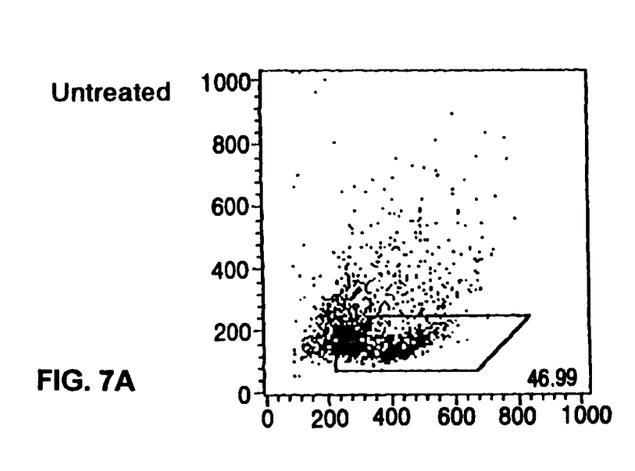
FIGS. 7A–7D. Histograms showing the number of 70Z/3 cells treated with ( 300 (M NAD for 18 hours on the Y-axis and propidium iodide fluorescence on the X-axis. The left peak is cells in G0/G1 and the right peak with twice the amount of fluorescence is cells in G0/M. Cells between the two peaks are going through S-phase.
Figure 7B:
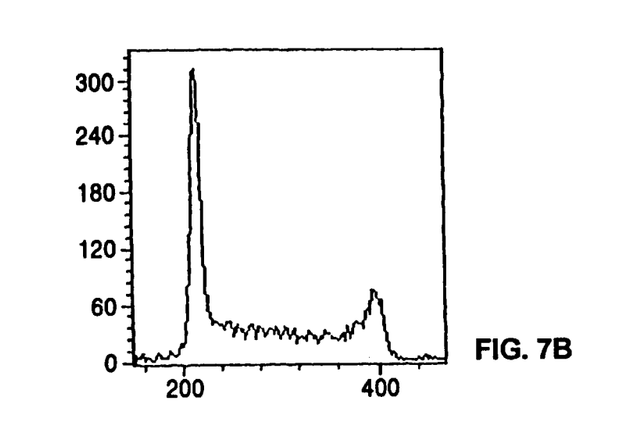
Figure 7C:
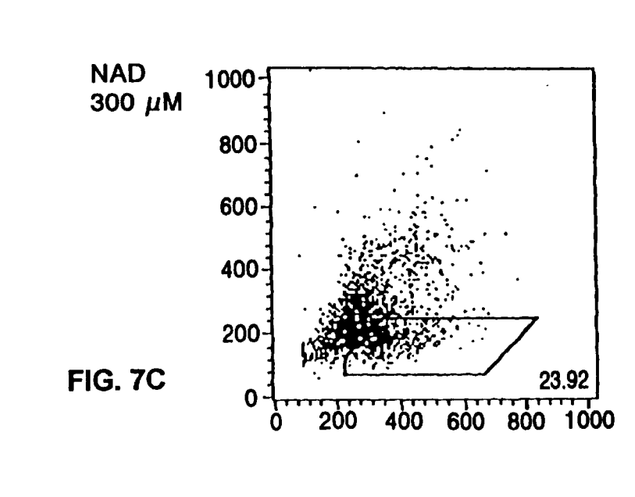
Figure 7D:
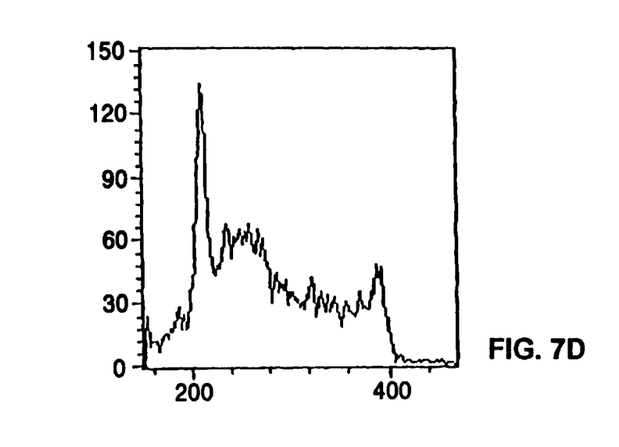

This example demonstrates the ability of NAD analogs to sensitize the cytotoxic effects of ionizing radiation. FIGS. 6A and 6B displays the clonogenic cytotoxicity of NAD administered within the dose range of 0–500 µM ±radiation. Because the radiation +NAD dose response curve had a negative slope with a greater clonogenic cytotoxicity than either agent separately, then the observed sensitized effects were additive to synergistic through the dose range evaluated. These data were taken as evidence that NAD and its analogs could be expected to sensitize conventional therapies such as radiation where DNA induction is an important part of their mode of action.

EXAMPLE 6

It has already been reported in the literature that adenosine-containing compounds can imbalance nucleotide pools and as such are useful in the treatment of neoplastic, fungal and parasitic diseases (see citations in Summary of Invention Section). This example teaches that NAD is also a potent cell cycle blocking agent accumulating cells in S-phase. FIGS. 7A–7D show that the histogram of untreated 70Z/3 cells displays a typical 200 cell region G0/G/1 peak and a 400 cell region G2/M peak. The S-phase cells located between these two peak regions were very low. However, cells exposed to 300 µM NAD showed an appreciable accumulation of cells in S-phase. These data teach that NAD can function as a prodrug for the uptake of adenosine-containing agents via binding to NADases (ADP-ribose cyclases) and as such can function as an antimetabolite imbalancing nucleotide pools and inducing cytotoxicity by anti-proliferation. This property of NAD has never before been described even though it is one of the most important and well known metabolites in cells. Therefore, this discovery is unusually novel over prior art, and as such it is inventive.

EXAMPLE 7

Figure 8:
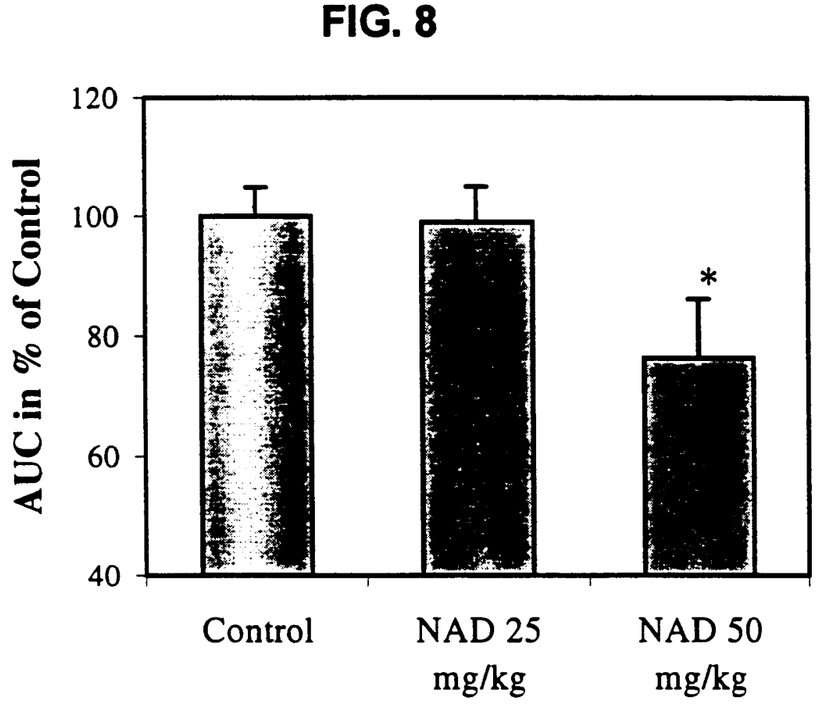
FIG. 8. Scid mice (n=10 per group) xenografted with a human lung adenocarcinoma (H2981) were treated i.p. with (daily doses of 5×25 or 50 mg/kg NAD per week for 21 days. Initial tumor volumes were 80–100 mm2 and area under the curve (AUC) tumor growth values were calculated and analyzed as described previously (Hua et al, Anti-Cancer Drugs 6: 451–455, 1995). *=p<0.05 by t-test compared to controls.

The data presented in FIG. 8 evaluate NAD as a direct acting antitumor drug. Here it is disclosed that scid mice xenografted with a human adenocarcinoma (H2981) and administered daily doses of NAD at 50 mg/kg have shown a significant (p<0.05) reduction in tumor growth compared to untreated controls or to a lower dose of NAD treatment (25 mg/kg). There was also no significant body weight loss or acute symptoms relating to NAD treatment indicating a lack of any toxic side effects. These results teach the enablement and utility of using NAD as a chemotherapeutic drug. Moreover, the dose response effect of NAD in controlling tumor growth establish a non-toxic efficacious dose range for future extrapolation from rodent tumor models into humans.

What is claimed is:
1. A method of killing tumor cells or fungal or parasitic microorganisms which comprises contacting the tumor cells or the fungal or parasitic microorganisms with an amount of nicotinamide or a pyridine analog thereof that is linked to ADP-ribose or a structure-modified analog thereof selected from the group consisting of cyclic ADP-ribose, 2' and 3' deoxy ADP-ribose, such that, when NADase hydrolyzes said nicotinamide or said pyridine analog thereof free from said ADP-ribose or said structure-modified analog thereof, said ADP-ribose or said structure-modified analog thereof is selectively internalized into said tumor cells or said fungal or parasitic microorganisms in an amount effective to increase clonogenic toxicity of said tumor cells or said fungal or parasitic microorganisms.

2. The method of claim 1 wherein said pyridine analog of nicotinamide is 3-acetyl pyridine.

3. The method of claim 2, wherein the subject is an animal.

4. The method of claim 2, wherein the subject is a human.

5. A method of killing tumor cells or fungal or parasitic microorganisms which comprises contacting the tumor cells or the fungal or parasitic microorganisms with an amount of nicotinamide adenine dinucleotide or an analog of nicotinamide adenine dinucleotide selected from the group consisting of ADP-ribose 2' deoxy NAD, 3' deoxy NAD and 3-acetyl pyridine adenine dinucleotide effective to increase clonogenic toxicity of said tumor cells or said fungal or parasitic microorganisms.

6. A method of killing tumor cells or fungal or parasitic microorganisms in a subject which comprises administering to the subject an amount of nicotinamide adenine dinucleotide or an analog of nicotinamide adenine dinucleotide selected from the group consisting of ADP-ribose 2' deoxy NAD, 3' deoxy NAD and 3-acetyl pyridine adenine dinucleotide effective to increase clonogenic toxicity of said tumor cells or said fungal or parasitic microorganisms.

* * * * *